(12) United States Patent
Lira et al.

(10) Patent No.: US 6,610,905 B1
(45) Date of Patent: Aug. 26, 2003

(54) TRANSGENIC MOUSE MODEL FOR KAPOSI'S SARCOMA

(75) Inventors: Sergio A. Lira, Chatham, NJ (US); Tong-Yuan Yang, Belle Mead, NJ (US)

(73) Assignee: Schering Corporation, Kenilworth, NJ (US)

( * ) Notice: Subject to any disclaimer, the term of this patent is extended or adjusted under 35 U.S.C. 154(b) by 218 days.

(21) Appl. No.: 09/619,334

(22) Filed: Jul. 19, 2000

Related U.S. Application Data

(60) Provisional application No. 60/144,964, filed on Jul. 21, 1999.

(51) Int. Cl.[7] .................. G01N 33/00; C12P 21/00; A01K 67/00; A01K 67/033; C12N 15/00
(52) U.S. Cl. .................. 800/11; 800/3; 800/4; 800/8; 800/13; 800/18; 800/21
(58) Field of Search .................. 800/8, 3, 4, 11, 800/13, 18, 21

(56) References Cited

U.S. PATENT DOCUMENTS

| | | | |
|---|---|---|---|
| 4,736,866 A | 4/1988 | Leder et al. | 800/1 |
| 5,877,399 A | 3/1999 | Hsiao et al. | 800/2 |

FOREIGN PATENT DOCUMENTS

| | | | |
|---|---|---|---|
| WO | WO 98/51781 | 11/1998 | C12N/5/00 |

OTHER PUBLICATIONS

Mullins et.al.; Perspectives Series: Molecular Medicine in Genetically Engineered Animals, 1996, J. Clin. Invest., vol. 97: 1557–1560.*
Ebert et.al.; A Moloney MLV–Rat Somatotropin Fusion Gene Produces . . . in a Transgenic Pig, 1988, Molecular Endocrinology 2: 277–283.*
Hammer et.al.; Genetic Engineering of Mammalian Embryos, 1986, J. Anim. Sci. 63: 269–278.*
Wall et.al.; Transgenic Dairy Cattle: Genetic Engineering on a Large Scale, 1997, J Dairy Sci. 80: 2213–2224.*
Sodhi et.al.; The Kaposi's Sarcome–associated Herpes Virus G Protein–coupled Receptor . . . Acting on Hypoxia–inducible Factor 1, 2000, Cancer Research 60: 4873–4880.*
Bello et.al.; The human herpesirus–8 ORF 57 gene and its properties, 1999, Journal of General Virology 80: 3207–3215.*
Birkmann et.al.; Cell Surface Heparan Sulfate Is a Receptor for Human Herpesvirus 8 and IInteracts with Envelope Glycoprotein K8.1, 2001, Journal of Virology : 11583–11593.*
Mercader et.al.; Induction of Human Immunodeficiency Virus 1 Replication by Human Herpesvirus 8, 2001, Arch Pathol Lab Med , vol. 125: 785–789.*
Lebbe et.al.; Charaterization of in vitro culture of HIV–negative Kaposi's sarcoma–derived cells. In vitro responses to alfa interferon 1997, Abstract.*
Lira, Sergio A. et al., "An Upstream Region of the Mouse ZP3 Gene Directs Expression of Firefly Luciferase Specifically to Growing Oocytes in Transgenic Mice", *Proc. Natl. Acad. Sci., USA,* 87:7215–7219, (Sep. 1990).
Nakamura, Shuji et al., "Vascular Endothelial Growth Factor Is A Potent Angiogenic Factor in AIDS–Associatd Kaposi's Sarcoma–Derived Spindle Cells", *The Journal of Immunology* 158:4992–5001 (1997).
Bais, Carlos et al., "G–Protein–Coupled Receptor of Kaposi's Sarcoma–Associated Herpesvirus Is A Viral Oncogene and Angiogenesis Activator", *Nature* 391:86–89 (Jan. 1, 1998).
Detmar, Michael et al., "Increased Microvascular Density and Enhanced Leukocyte Rolling and Adhesion in the Skin of VEGF Transgenic Mice", *J. Invest. Dermatol.* 111:1–6 (1998).
Larcher, Fernando et al., "VEGF/VPF Overexpression In Skin of Transgenic Mice Induces Angiogenesis, Vascular Hyperpermeability and Accelerated Tumor Development", *Oncogene* 17:303–311 (1998).
Yang et al., "Transgenic Expression of the Chemokine Receptor Encoded by Human Herpesvirus 8 Induces and Angioproliferative Disease Resembling Kaposi's Sarcoma", *J. Exp. Med.,* vol. 191, pp. 445–453 (2000).

* cited by examiner

*Primary Examiner*—Deborah Crouch
*Assistant Examiner*—Joseph Woitach
(74) *Attorney, Agent, or Firm*—Michael G. Biro; Jaye P. McLaughlin; Immac J. Thampoe

(57) ABSTRACT

The present invention relates to a non-human transgenic mouse containing a constitutively active G-protein coupled receptor, which produces Kaposi's sarcoma-like symptoms. The transgenic mouse is useful in identification of reagents for the prevention, treatment and/or cure of diseases related to production of proliferative vascular lesions, including Kaposi's sarcoma.

8 Claims, No Drawings

TRANSGENIC MOUSE MODEL FOR KAPOSI'S SARCOMA

This application claims the benefit of Provisional Application No. 60/144,964 filed Jul. 21, 1999.

FIELD OF THE INVENTION

The present invention relates to transgenic animals and their use as a disease model system to study Kaposi's sarcoma and the effects of various therapeutic agents on disease onset and progression. The invention also relates to the use of transgenic animals as a molecular model in the study of vGPCR and molecules affected by vGPCR's action or which affect vGPCR's function.

BACKGROUND OF THE INVENTION

Kaposi's sarcoma was considered to be a rare tumor, but its incidence has dramatically increased with the AIDS epidemic and is at present the most common tumor associated with HIV infection. In 10 to 20% of HIV-1-infected patients, Kaposi's sarcoma has led to a significant morbidity from edema, lymphatic obstruction, organ infiltration and pulmonary dysfunction. Up to 30% of patients have died from complications of Kaposi's sarcoma.

Human herpesvirus 8 ("HHV8"), a γ-2 lymphotropic herpesvirus, appears to be the etiological agent associated with Kaposi's sarcoma (Ganem, 1997, *Cell* 91:157–160; Greenblatt, 1998 *Infect. Dis. Clin. North Am.* 12:63–82), but its role in Kaposi's sarcoma pathogenesis has remained an enigma (Gallo, 1998 *Science* 282:1837–1839). The present invention provides a key link between HHV8 and Kaposi's sarcoma pathogenesis. HHV8 infects malignant and progenitor cells of Kaposi's sarcoma, it encodes putative oncogenes and genes that may cause Kaposi's sarcoma pathogenesis by stimulating angiogenesis. The G-protein-coupled receptor (vGPCR) encoded by an open reading frame (ORF 74) of HHV8 is expressed in Kaposi's sarcoma lesions and stimulates signaling pathways constitutively linked to cell proliferation and cell death.

Understanding the role of vGPCR in HHV-8 replication and its overall function in the development of Kaposi's sarcoma has been hampered by the lack of an in vivo model. It is therefore an object of the present invention to generate a transgenic animal expressing vGPCR. This transgenic animal represents and important new tool to further dissect the pathogenesis of Kaposi's sarcoma.

SUMMARY OF THE INVENTION

The present invention relates to the identification of a model system to study Kaposi's sarcoma and other similar diseases.

A transgenic non-human animal model for disease and molecular mechanism is provided, together with methods and compositions for preparation of the animal model and methods for using it. The invention provides a transgenic non-human animal whose genome comprises a constitutively active G-coupled receptor protein transgene comprising regulatory sequences from a promoter operably linked to a coding sequence, wherein expression of said transgene produces Kaposi's sarcoma-like symptoms.

The invention also provides a transgenic non-human animal embryo whose somatic and germ cells contain a gene encoding a constitutively active G-protein coupled receptor.

The invention further provides a method for producing a non-human animal having somatic and germ cells that contain an HHV8 gene encoding a constitutively active G-protein coupled receptor which comprises the steps of introducing multiple copies of an expression cassette into the non-human mammal at an embryonic stage, and developing the embryo to term in a pseudo-pregnant foster female. The expression cassette comprises a human herpesvirus 8 gene encoding a chemokine receptor sequence operably joined to regulatory sequences for expression of the coding sequence in hematopoietic cells. The resulting transgenic non-human mammals develop Kaposi's sarcoma-like lesions in multiple organs, which are characterized by one or more of the symptoms including intense angiogenic activity, presence of spindle and inflammatory cells, and expression of vGPCR, CD34 and VEGF.

The transgenic animals are useful, for example, in screening protocols for agents which can be used for treatment and/or prevention of Kaposi's sarcoma and diseases/conditions associated with vGPCR, CD34 or VEGF.

DETAILED DESCRIPTION OF THE INVENTION

In order that the invention described herein may be more fully understood, the following detailed description is set forth. All references cited herein are incorporated in their entirety by reference.

The present invention provides a non-human transgenic animal which is heterozygous for a functional HHV8 gene encoding a chemokine receptor, including a constitutively active G-protein coupled receptor (vGPCR) that binds several CC and CXC chemokines or homologues thereof. As used herein, functional is used to describe a gene or protein that, when present in a cell or in vitro system, performs normally as if in a native or unaltered condition or environment.

The animals of this invention are useful for the study of the tissue and temporal specific expression or activity of vGPCR in animals having a functional copy of the gene. The animals are also useful for studying the ability of a variety of compounds to act as modulators of vGPCR activity or expression in vivo or, by providing cells for culture, in vitro. As used herein, a modulator is a compound that causes a change in the expression or activity of vGPCR, or causes a change in the effect of the interaction of vGPCR with its ligand(s), or other protein(s).

In reference to the transgenic animals of this invention, "transgenes" or "genes" will be referred to. As used herein, a transgene is a genetic construct including a gene. The transgene is integrated into one or more chromosomes in the cells in an animal by methods know in the art. Once integrated, the transgene is carried in at least one place in the chromosomes of the transgenic animal. A gene is a nucleotide sequence that encodes a protein. The gene and/or transgene may also include genetic regulatory elements and/or structural elements known in the art.

Another aspect of the invention is a non-human animal embryo carrying the gene encoding vGPCR. This embryo is useful in studying the effects of Kaposi's sarcoma in the developing animal. In particular embodiments, the animal is a mouse. The animal embryo is also a source of cells carrying a functional vGPCR gene.

The present invention is further directed to a transgenic non-human eukaryotic animal, preferably a rodent, such as a mouse or other animal capable of developing detectable characteristics from the expression of vGPCR. The animal expresses vGPCR sequence in hematopoietic cells such that the animal develops Kaposi's sarcoma-like lesions in one or more organs, including for example, intense angiogenic activity, presence of spindle and inflammatory cells, teleangiectasia, erythematous maculae, plaques or tumors, or expression of vGPCR, CD34 or VEGF within a short period of time from birth, generally within a year from birth, preferably within 1 to 4 months from birth. The vGPCR sequence is introduced into the animal, or an ancestor of the animal, at an embryonic stage, preferably the one cell, or fertilized oocyte stage and generally not later than about the 8-cell stage. The zygote or embryo is then developed to term in a pseudo-pregnant foster female. The vGPCR genes are introduced into an animal embryo so as to be chromosomally incorporated in a state which results in super-endogenous expression of the vGPCR protein and the development of a Kaposi's sarcoma-like disease. The proliferative vascular lesions in affected transgenic animals are indicative of a Kaposi's sarcoma-like disease.

The present invention offers several advantages over existing models for progressive vascular lesions, characterized in Kaposi's sarcoma-like disease. The vascular lesions are often multicentric and seen in the skin, heart, skeletal muscle and submucosa and tunica muscularic of the small and large intestine. These lesions often consisted of dilated thin-walled blood vessels lined by normal or plump endothelial cells and spindle-shaped cells surrounding irregular vascular channels containing erythrocytes. Cellular pleomorphism may also be seen in more extensive lesions, but mitotic figures are rare. Scattered throughout the vascular lesions, hemosiderin deposits and variable numbers of mixed inflammatory cells may be seen, including macrophage, eosinophils, mast cells, neutrophils and lymphocytes. At the molecular level, VEGF expression appears to be correlated with expression of vGPCR. These changes provide a particular advantage in screening protocols for agents which can be used in the treatment of progressive vascular diseases such as Kaposi's sarcoma. Because many of these results can be observed in live animals, it is unnecessary to wait until the animal is sacrificed to determine whether the agent is effective for its intended purpose.

Transgenic animals of the invention are constructed using an expression cassette which includes in the 5'-3' direction of transcription, a transcriptional and translational initiation region associated with gene expression in hematopoietic cells, DNA encoding a mutant or wild-type vGPCR protein and a transcriptional and translational termination region functional in the host animal. One or more introns may also be present. For expression, of particular interest are promoters which provide for preferential or at least substantially specific expression in hematopoietic cells as compared to other tissue. By "at least substantially" is intended that expression in hematopoietic cells is greater than about 10-fold than in other cell types. The promoters can be endogenous to the host animal or foreign or exogenous to the host animal. By "foreign" is intended that the promoter is not found in the wild-type animal host into which the promoter is introduced. By "endogenous" is intended sequences both indigenous (i.e. natural to) the host animal and those present in the host animal as a result of an infectious disease, e.g. viral, prion, and the like.

A promoter from a gene expressed in hematopoietic tissues, such as thymus, spleen, lymph nodes, blood or bone marrow of the host animal is preferably employed for varying the phenotype of the host animal. The transcriptional level should be sufficient to provide an amount of RNA capable of producing a modified animal. By "modified animal" within the subject invention is meant an animal having a detectably different phenotype from a non-transformed animal of the same species, for example one not having the transcriptional cassette including VGPCR coding sequences in its genome. Preferably, the promoter is a strong promoter which drives a high level of expression of the vGPCR coding sequence in the target cells and/or which provides for many copies of the coding sequence in target cells.

The promoter preferably comprises a regulatory region for transcriptional initiation and a regulatory region for translational initiation of untranslated 5' sequences, "ribosome binding sites", responsible for binding mRNA to ribosomes and translational initiation. The transcriptional initiation regulatory region may be composed of cis-acting elements which activate or repress transcription in response to binding of transacting factors present in varying amounts in different cells. It is preferred that all of the transcriptional and translational functional elements of the initiation control region are derived from or obtainable from the same gene. In some embodiments, the promoter is modified by the addition of sequences, such as enhancers, or deletions of non-essential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

Tissue-specific transcription suggests that gene regulatory proteins are bound to enhancer sequences and other upstream promoter elements. By enhancer element ("enhancer") is intended a regulatory DNA sequence that is capable of activating transcription from a promoter linked to it with synthesis beginning at the normal RNA start site; which is capable of operating in both orientations (normal or flipped); and which functions even when moved either upstream or downstream from the promoter. Both enhancers and other upstream promoter elements bind sequence specific DNA binding proteins that mediate their effects. To identify the exact nucleotide sequences important for the function of the enhancer(s), and other upstream elements, fragments of the untranslated 5' region encoding a protein expressed in a tissue of interest are screened for their capacity to bind nuclear proteins and for their ability to function with a heterologous promoter.

Binding experiments with nuclear proteins from hematopoietic cells, bone marrow, spleen, lymph nodes, blood or thymic cells can be used to determine the presence of enhancer or silencer sequences; the protein binding studies can be used to pinpoint specific nucleotide sequences that bind to a corresponding series of gene regulatory proteins.

A variety of promoter sequences can be used to control the expression of vGPCR coding sequences. One particularly preferred promoter is the human CD2 promoter (Zhumabekov T. et al., 1995, J. Immunol Methods 185 (1):133–40). Other useful promoters include the metallothionine (MT) promoter from which expression can be regulated through modulation of zinc and glucocorticoid hormone levels (Palmiter, et al., 1982, *Nature* 300:611–615); the human β-actin gene promoter (Ray, et al., 1991 *Genes & Devel.* 5:2265–2273); the human platelet derived growth factor B (PDGF-B) chain gene promoter (Sasahara, et al., 1991, *Cell* 64:217–227); the human copper-zinc superoxide dismutase gene promoter (Ceballos-Picot, et al., 1991 Brain Res. 552:198–214); and promoters for members of the mammalian POU-domain regulatory gene family (Xi, et al., 1989 Nature 340:3542). The POU-domain is the region of similarity between the four mammalian transcription factors Pit-1, Oct-1, Oct-2, and Unc-86, and represents a portion of the DNA-binding domain. These promoters provide for expression specifically with the hematopoietic cells and ultimately within the vascular, bone and thymic systems of the transgenic animals. The chicken beta-actin promoter with cytomegalovirus immediate-early gene enhancer will direct ubiquitous expression of the transgene within a variety of tissues (Okabe et al., 1997, *FEBS Letters* 407:313–319.

Any animal can be used as a source of fertilized egg cells or embryonic stem cells, although generally the preferred host animal is one which lends itself to multi-generational studies. Other preferred characteristics of the host animal include that it does not die at such an early age while it expresses high levels of vGPCR that there is insufficient time for observable pathological changes to occur. Of particular interest are rodents, including mice. There are several commercially available strains of mice, such as mice of the FVB strain and crossed commercially available strains such as the (C57BL6)×(SJL.F1) hybrid and the (C57BL6J×DBA/2J) hybrid. The latter parental line also is referred to as B6D2. Other strains and cross-strains of animals can be evaluated using the techniques described herein for suitability for use as a model for progressive vascular diseases such as Kaposi's sarcoma. In some instances, however, a primate, for example, a rhesus monkey may be desirable as the host animal, particularly for therapeutic testing.

Transgenic mammals are prepared in a number of ways. A transgenic organism is one that has an extra or exogenous fragment of DNA in its genome. In order to achieve stable inheritance of the extra or exogenous DNA fragment, the integration event must occur in a cell type that can give rise to functional germ cells, either sperm or oocytes. Two animal cell types that can form germ cells and into which DNA can be introduced readily are fertilized egg cells and embryonic stem cells. Embryonic stem (ES) cells can be returned from in vitro culture to a "host" embryo where they become incorporated into the developing animal and can give rise to transgenic cells in all tissues, including germ cells. The ES cells are transfected in culture and then the mutation is transmitted into the germline by injecting the cells into an embryo. The animals carrying mutated germ cells are then bred to produce transgenic offspring.

A preferred method for making the subject transgenic animals is by zygote injection. This method is described, for example in U.S. Pat. No. 4,736,866. The method involves injecting DNA into a fertilized egg, or zygote, and then allowing the egg to develop in a pseudo-pregnant mother. The zygote can be obtained using male and female animals of the same strain or from male and female animals of different strains. The transgenic animal that is born is called a founder, and it is bred to produce more animals with the same DNA insertion. In this method of making transgenic animals, the new DNA typically randomly integrates into the genome by a non-homologous recombination event. One to many thousands of copies of the DNA may integrate at one site in the genome.

Generally, the DNA is injected into one of the pronuclei, usually the larger male pronucleus. The zygotes are then either transferred the same day, or cultured overnight to form 2-cell embryos and then transferred into the oviducts of the pseudo-pregnant females. The animals born are screened for the presence of the desired integrated DNA. By a pseudo-pregnant female is intended a female in estrous who has mated with a vasectomized male; she is competent to receive embryos but does not contain any fertilized eggs. Pseudo-pregnant females are important for making transgenic animals since they serve as the surrogate mothers for embryos that have been injected with DNA or embryonic stem cells.

Putative founders are screened for the presence of the transgene by PCR analysis of tail DNA as described in Example 1. Transgene expression was initially evaluated by RNA analysis using the Northern blot technique. Preferably, VGPCR transcripts may be detected in thymus and bone marrow of transgenic but not control mice. To ascertain the expression of vGPCR at the cell surface, binding experiments can be performed using transgenic and control thymocytes. To this end, labeled human interferon-γ-inducible protein (hIP-10) was employed. The results of this experiment (for details, see Example 2) demonstrate that transgenic thymocytes express VGPCR within hematopoietic cells of the transgenic mice. The transgenic animals also are observed for clinical changes. Examples of visible indications of expression of VGPCR include teleangiectasia, erythematous maculae and plaques and tumors on the ears, tail and/or nose. Further, the transgenic animals may also show diffuse erythema and teleangiectasia of the skin accompanied by dramatic swelling of the paws. Internal organs may also be affected as erythematous exophytic lesions may be seen in the wall of the small and large intestine. Histopathologically, the animals may be observed to carry a spectrum of proliferative vascular lesions which resemble those observed in Kaposi's sarcoma The vascular lesions may be multicentric and seen predominantly in the skin (i.e. tail, nose, and ears), heart, skeletal muscle and submucos and tunica muscularis of the small and large intestines.

It is a theory of the invention that parameters that can influence the phenotype of transgenic animals include the host strain, the primary structure of the vGPCR and the levels of vGPCR expression; the clinical changes observed in transgenic animals are a result of a combination of these factors. For a particular strain and a particular coding sequence, sufficient copies of a vGPCR gene and/or a sufficient level of expression of a coding sequence derived from a particular vGPCR gene which will result in observable clinical symptoms, together with a measurable biochemical change in relevant vascular structures can be determined empirically. By sufficient copies is intended that the total expression level from each construct is at least two-fold, preferably at least two to four-fold, more preferably five-fold or greater than that of an endogenous native gene, or that the overall copy number is such as to achieve this relative increase. In some instances, two to four copies of the gene, especially of a mutated disease-linked gene, are sufficient to achieve a desired relative increase in vGPCR, while in other instances, particularly where a native gene is used, a larger copy number may be required. Native gene in the context of the present invention includes other constitutively active G-coupled protein receptors present in the host animal. The copy number may range from five copies to more than 60 copies, depending on the species of vGPCR expressed and the particular disease-associated mutations in the vGPCR gene.

The founder animals can be used to produce stable lines of transgenic animals that superexpress VGPCR, either mutant or non-mutated vGPCR. For ease of propagation, male founder mice are preferred. The animals are observed clinically. Analyses of transgene copy number (to exclude multiple transgene insertion sites), mRNA expression and protein expression in these animals are also performed. These studies provide information about the age of onset of illness, the duration of illness, the penetrance of the phenotype, the range of pathologic findings and the dependence of phenotype upon levels of protein expression.

The animals of the present invention can be used as tester animals for materials of interest, e.g. chemotherapeutic agents or anti-viral agents to prevent and/or treat Karposi's sarcoma-like diseases. An animal is treated with the material of interest, and a reduced incidence or delayed onset of vascular disease, as compared to untreated animals, is detected as an indication of protection and/or response to treatment. The indices used preferably are those which can be detected in a live animal, such as development or progression of skin lesions. The effectiveness can be confirmed by effects on pathological changes when the animal dies or is sacrificed. The animals further can be used as tester animals for materials of interests that improve or cure Kaposi's sarcoma-like diseases. An animal with vascular disease is treated with the material of interest, and a delayed death, or improvement in vascular disease as compared to the untreated animal, is detected as an indication of amelioration or cure.

The animals of the invention may also be used as models for the molecular mechanism of Kaposi's sarcoma-like diseases. For example, it is shown here that VEGF may induce the development of the vascular lesions associated with Kaposi's sarcoma, but it is likely that other, yet unknown factors are involved in the phenotypes observed in the transgenic mice because transgenic animals expressing VEGF (Nakamura et al., 1997, *J. Immunol.* 158:4992–5001; Larcher et al, 1998, *Oncogene* 17:303–11) do not display identical phenotypes to those described herein. The vascular lesions of the transgenic animals of the invention may be used as a source for RNA expressing novel factors, which can be purified from the vascular lesions and screened against micro-arrays. In this way, novel growth factors which play a role in the pathology of Kaposi's sarcoma may be identified.

In order that this invention be more fully understood, the following examples are set forth. These examples are for the illustrative purposes only and are not to be construed as limiting the scope of this invention in any way.

EXAMPLE 1

Generation of Transgenic Animals

Transgenic mice expressing vGPCR under the control of the human CD2 promoter were generated (Zhumabekov, et al., 1995, *J. Immunol. Meth.* 185:133–140). The coding sequence for vGPCR was amplified from the genomic DNA of BC-1 cells (American Type Culture Collection Accession No. U75698) with the following primers:

TY42(5'-GGAATTCACCACCATGGCGGCCG AGGATTTCC-3' (SEQ ID NO: 1)) and

TY10(5'-ATCCTGCAGGGGCTACGTGGTGGC GCCGGACAT-3' (SEQ ID NO: 2)).

Sequencing of the amplified fragment showed it to be identical to the gene described by Chang et al. (1994, *Science* 266:1865–1869). The 1.0 kb vGPCR fragment was cloned into EcoRI-SmaI sites of a plasmid containing the human CD2 enhancer/promoter and locus control region (LCR)(Zhumabekov, et al., 1995, *J. Immunol. Meth.* 185:133–140). Generation and genotypic analyses of the animals were done as previously described (Lira, et al., 1990, *Proc. Natl. Acad. Sci. USA* 8:7215–7219). The plasmid was microinjected into the male pronucleus of fertilized mouse [(C57BL/6J X DBA/2)F$_2$; The Jackson Laboratory] eggs. Microinjected eggs were then transferred into oviducts of CD-1 (Charles River Breeding Laboratories) foster mothers according to published procedures (Hogan et al., 1986, *Manipulating the Mouse Embryo: A Laboratory Manual* (Cold Spring Harbor Laboratory, Cold Spring Harbor, N.Y.).

To identify the transgenic founders the following primers were used: 5'-TGG-AAC-GTT-GGA-ATA-CTC-TCT-CTG-3' and 5'-AGG-TAC-CTC-ACT-AGA-CTG-ACG-CAC-3'. As internal control for the reactions primers designed to amplify a segment of the mouse LDL gene were used: 5'-ACC CCA AGA CGT GCT CCC AGG ATG A-3' and 5'-CGC AGT GCT CCT CAT CTG ACT TGT-3'. The following PCR conditions were used: $94^c$ for 3 min, then 30 cycles of $94^c$, 30 sec; $60^c$, 30 sec and $72^c$, 1 min. A final step of $72^c$ for 7 min was added at the end of the 30 cycles. The integration of the transgene in the mouse genome will lead to amplification of a 250bp DNA fragment. Amplification of the LDL gene will yield a 383bp DNA fragment.

The resulting transgenic animals were kept under pathogen-free conditions. Seven transgenic founders were obtained from which five transgenic lines were derived.

EXAMPLE 2

Molecular Analysis of the Transgenic Phenotype

Transgene expression was initially evaluated by Northern blot analysis. RNA was extracted from tissues using Ultraspec RNA, following specifications from the manufacturer (Biotecx). Total RNA (20 µg) was denatured and blotted onto GeneScreen membrane (NEN). A 1.0 kb fragment of the vGPCR DNA was radiolabelled and was used as a probe in these experiments. For RT-PCR, cDNA was synthesized from 2 µg total RNA primed with oligo-(dT) using the Superscript II Preamplification System (GIBCO-BRL). Two to five microliters of cDNA was amplified in a 50 µl reaction volume with the following conditions: 94° C. for 1 min then 35 cycles at 94° C. for 1 min, 72° C. for 1.5 min, 72° C. for 2 min, incubated in a Gene Amp PCR System (Perkin Elmer Cetus). The oligonucleotide primers corresponding to the sense and antisense strands, respectively, were as follows:

vGPCR, 5'-ATGGCGGCCGAGGATTTCCTAACC-3' (SEQ ID NO: 3) and 5'-AGGTACCTCACT AGACTGACGCAC-3' (SEQ ID NO: 4);

G3PDH, 5'-TGAAGGTTCGGTGTGAACGGATTTGGC-3' (SEQ ID NO: 5) and 5'-CATGTAAGGCCA TGAGGTCCACCAC-3' (SEQ ID NO: 6).

The final PCR products were analyzed on a 2% agarose gel containing ethidium bromide. These Northern blot analyses showed that vGPCR transcripts could be detected in thymus and bone marrow of transgenic but not control mice, a finding consistent with the pattern of transgene expression driven by the CD2 promoter (Lang, et al., 1988, *EMBO J.* 7:1675–1682).

To ascertain the expression of vGPCR at the cell surface, binding experiments were performed using transgenic and control thymocytes. To this end, labeled human interferon-γ-inducible protein (hIP-10) was used, since it has been demonstrated that this chemokine inhibits vGPCR constitutive signaling (Geras-Raaka, et al., 1998, *J. Exp. Med.* 188:405408). Thymocytes (1,000,000 cells/point) were resuspended in binding buffer (50 mM HEPES, 1 mM CaCl$_2$, 5 mM MgCl$_2$, 0.5% BSA) and incubated with 0.1 nM radiolabelled human IP-10 (NEN Life Science Products) in the presence of unlabeled chemokines in 96-well plates.

After two hours at room temperature, plates were spun down and cell pellets were resuspended in binding buffer supplemented with 0.5 M NaCl. Cells were spun through 10% glycerol in binding buffer with 0.5 M NaCl. Cell pellets were frozen in liquid nitrogen, clipped and counted. All experiments were performed in triplicate. Thymocytes from transgenic mice showed more than a 5-fold increase of binding of radiolabelled hIP-10 compared to control thymocytes. Binding of hIP-10 to transgenic thymocytes was competed off by unlabeled hIP-10. The increased binding of hIP-10 to transgenic thymocytes was not due to binding to its murine homologue receptor, CXCR3, because mCXCR3 expression was not detected in transgenic thymuses by Northern blot analysis. These results confirm the expression of vGPCR within hematopoietic cells of the transgenic mice.

EXAMPLE 3

Pathological and Histological Analysis of the Transgenic Phenotype

Mice expressing vGPCR were normal at birth. However, within the first 30–90 days of life, transgenic mice from three independent lines (9. 19 and 122) developed lesions which were remarkably similar to those seen in Kaposi's sarcoma patients. These mice developed teleangiectasia, erythematous maculae, plaques and tumors on their ears, tails and noses. Furthermore, the animals showed diffuse erythema and teleangiectasia of the skin accompanied by dramatic swelling of the paws. Moreover, internal organs were also affected as erythematous exophytic lesions were seen in the wall of the small and large intestine.

For histological analysis, tissues were either fresh frozen for cryosection, or were fixed, processed and stained with hematoxylin and eosin (H&E). The transgenic mice had a spectrum of proliferative vascular lesions which resembled those observed in Kaposi's sarcoma. The vascular lesions were multicentric and were seen in the skin (tail, nose and ears), heart, skeletal muscle and submucosa and tunic muscularis of the small and large intestines. The vascular lesions consisted of dilated thin-walled blood vessels lined by normal or plump endothelial cells and spindle-shaped cells surrounding irregular vascular channels containing erythrocytes. Cellular pleomorphism was prominent in the more extensive lesions, but mitotic figures were rare. The edges of the more extensive lesions were irregular, with projections of cells into surrounding tissue. Scattered throughout the vascular lesions were hemosiderin deposits and variable numbers of mixed inflammatory cells, including macrophages, eosinophils, mast cells, neutrophils and lymphocytes.

EXAMPLE 4

Immunohistochemistry of the Transgenic Animals

Cells present in the lesions were next analyzed by RT-PCR for their ability to express the transgene. Transgene transcripts were detected in samples with gross lesions (ear, muscle), but not in transgenic samples not containing such lesions. To further study the expression of the transgene within the lesions, in situ hybridization with a riboprobe specific for vGPCR was performed. In situ hybridization was carried out as described in Lugo, et al. (1989, *Mol. Endocdnol.* 3:1313–1324). Sense and antisense $^{32}$P-labeled riboprobes were transcribed from cDNA templates of vGPCR (from nucleotides #473–1075) or VEGF (from nucleotide #91–429) with either T7 or T3 polymerase (Boehringer Mannheim). Cells expressing VGPCR were found in the lesions, but not in the adjacent parenchyma. The presence of cells expressing VGPCR within the lesions contribute to the development of the Kaposi's sarcoma lesions. Recently Bais et al demonstrated that VGPCR induces in vitro expression of VEGF, a potent angiogenic factor (Bais, et al., 1998, Nature 391:86–89) and its expression in transgenic mice leads to the development of angiogenic and inflammatory lesions which resemble those described in Example 3.

To determine whether there was expression of VEGF within the transgenic lesions, in situ hybridization was performed. It was found that VEGF was expressed by a few scattered cells within the lesions; a pattern of expression that resembled that of the transgene. These results suggest that cells expressing vGPCR may also express VEGF, and that VEGF may induce the development of the vascular lesions. It is unlikely, however, that VEGF accounts for all of the phenotypes observed in the transgenic mice because transgenic animals expressing VEGF do not display identical phenotypes to those described herein. Additional factors may thus be involved in the generation of the vascular lesions displayed herein.

EXAMPLE 5

Cellular Characteristics of the Transgenic Phenotype

These experiments utilized flow cytometry, which was carried out as follows. Cells from thymus, lymph nodes and blood were stained with anti-CD4, anti-CD8 monoclonal antibodies conjugated with PE or FITC (Pharmingen). Data were collected on a FACScan (Becton Dickinson) and analyzed using the CellQuest software.

Immune dysregulation appears to be a key feature in the pathogenesis of AIDS and organ transplant-associated Kaposi's sarcoma (Ensoli, et al., 1998, *Cytokine Growth Factor Rev.* 9:63–83). Interestingly, the transgenic mice presented marked changes in thymus, lymph nodes and peripheral blood. The transgenic thymuses had an abnormal architecture, with lack of distinct cortico-medullary borders, fewer Hassall's corpuscles, and multifocal accumulations of eosinophils, macrophages and neutrophils. Within the thymus, there was a significant accumulation (3 to 10-fold) of CD4/CD8 double negative cells ($p<0.05$) and a decrease in CD4/CD8 double positive cells ($p<0.05$). The numbers of CD4 and CD8 positive cells in the thymus, lymph nodes, and blood of the transgenic mice were also reduced. These abnormalities, which were consistently observed in animals from four different lines, clearly point to a developmental dysregulation of T cells which favors the development of the disease.

The data provided herein indicates that a single molecular entity in the HHV8 genome (vGPCR, the chemokine receptor homologue encoded by ORF 74) is sufficient to induce in mice, a spectrum of abnormalities that closely resemble those seen in patients with Kaposi's sarcoma; and suggest that these abnormalities are caused by shifts in the development, migration patterns and effector functions of hematopoietic cells expressing vGPCR. This transgenic model represents an important new tool to further dissect the pathogenesis of Kaposi's sarcoma.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to utilize the invention in various embodiments and with various modifications as are suited to the particular use contemplated. It is intended that the scope of the invention be defined by the claims appended hereto.

What is claimed is:

1. A transgenic mouse whose genome comprises:

a transgene comprising a human CD2 promoter operably linked to a nucleotide sequence encoding a polypeptide encoded by HHV8 ORF 74, and wherein expression of said transgene produces Kaposi's sarcoma-like symptoms.

2. A cell line derived from the transgenic mouse of claim 1.

3. A transgenic mouse embryo whose somatic and germ cells comprise a transgene comprising a human CD2 promoter operably linked to a nucleotide sequence encoding a polypeptide encoded by HHV8 ORF 74.

4. A method for producing a transgenic mouse comprising:

(a) providing a transgene comprising a human CD2 promoter operably linked to a nucleotide sequence encoding a polypeptide encoded by HHV8 ORF 74;

(b) introducing said transgene into embryonic stem cells;

(c) selecting embryonic stem cells containing said transgene;

(d) introducing said embryonic stem cells containing said transgene into mouse blastocysts;

(e) transplanting said blastocysts into a pseudopregnant mouse, and (f) allowing the embryo to develop to term, producing a chimeric founder transgenic mouse.

5. The method according to claim 4, wherein said introducing is by microinjection.

6. The method according to claim 4, which further comprises the step of:

(g) breeding chimeric transgenic mice with wild-type mice to obtain F1 mice heterozygous for said transgene.

7. A method for screening for an agent which ameliorates Kaposi's sarcoma-like symptoms, said method comprising:

comparing Kaposi's sarcoma-like symptoms of a first transgenic mouse contacted with said agent with that of a second transgenic mouse not contacted with said agent, wherein the genome of said first and said second transgenic mice each comprise a transgene comprising a human CD2 promoter operably linked to a nucleotide sequence encoding a polypeptide encoded by HHV8 ORF 74, wherein expression of said transgene in hematopoietic cells produces Kaposi's sarcoma-like symptoms, whereby an agent which ameliorates said symptoms is identified by decreased appearance of said symptoms in said first transgenic mouse in comparison with said second transgenic mouse.

8. The method of claim 7 wherein said Kaposi's sarcoma-like symptoms comprise teleangiectasia; erythematous maculeae; plaques or tumors; expression of vGPCR CD34 or VFGF; vascular lesions; tumors on the ears, tail and/or nose; diffuse erythema; and swelling of the paws.

* * * * *

```
                              SEQUENCE LISTING

<160> NUMBER OF SEQ ID NOS:  6

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Sense
      primer for vGPCR

<400> SEQUENCE: 1
ggaattcacc accatggcgg ccgaggattt cc                                   32

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Antisense
      primer for vGPCR

<400> SEQUENCE: 2
atcctgcagg ggctacgtgg tggcgccgga cat                                  33

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Sense
      primer for vGPCR

<400> SEQUENCE: 3
atggcggccg aggatttcct aacc                                            24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Antisense
      primer for vGPCR

<400> SEQUENCE: 4
aggtacctca ctagactgac gcac                                            24

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Sense
      primer for G3PDH

<400> SEQUENCE: 5
tgaaggttcg gtgtgaacgg atttggc                                         27

<210> SEQ ID NO 6
<211> LENGTH: 25
<212> TYPE: DNA
```

```
<213> ORGANISM: Artificial Sequence
<220> FEATURE:
<223> OTHER INFORMATION: Description of Artificial Sequence: Antisense
      primer for G3PDH

<400> SEQUENCE: 6
catgtaaggc catgaggtcc accac                                            25
```